United States Patent
Bureau et al.

(10) Patent No.: US 7,968,653 B2
(45) Date of Patent: Jun. 28, 2011

(54) MODIFICATION PROCESS FOR POLYMER SURFACES, NOTABLY FOR HYDROXYLATION OF POLYMER SURFACES AND PRODUCTS SO OBTAINED

(75) Inventors: Christophe Bureau, Juvisy-sur-Orge (FR); Jean Pinson, Fontenay-sous-Bois (FR)

(73) Assignee: Alchimer, Massy (FR)

( * ) Notice: Subject to any disclaimer, the term of this patent is extended or adjusted under 35 U.S.C. 154(b) by 0 days.

(21) Appl. No.: 12/089,960

(22) PCT Filed: Oct. 10, 2006

(86) PCT No.: PCT/FR2006/002270
§ 371 (c)(1),
(2), (4) Date: Jun. 13, 2008

(87) PCT Pub. No.: WO2007/042659
PCT Pub. Date: Apr. 19, 2007

(65) Prior Publication Data
US 2008/0249272 A1    Oct. 9, 2008

(30) Foreign Application Priority Data

Oct. 11, 2005  (FR) ..................................... 05 10371

(51) Int. Cl.
*C08F 8/06* (2006.01)
(52) U.S. Cl. .................. 525/370; 525/326.1; 525/333.7; 525/333.8; 525/360; 525/383; 525/387; 427/331; 427/337; 427/340; 427/341

(58) Field of Classification Search ................ 525/387, 525/333.7, 370
See application file for complete search history.

(56) References Cited

U.S. PATENT DOCUMENTS

| 3,925,178 A | | 12/1975 | Gesser et al. | |
| 4,740,282 A | * | 4/1988 | Gesser et al. | 204/165 |
| 5,618,887 A | * | 4/1997 | Bamford et al. | 525/279 |

FOREIGN PATENT DOCUMENTS

| EP | 0 300 232 A1 | 1/1989 |
| WO | 2004/043614 A1 | 5/2004 |

OTHER PUBLICATIONS

Aaron, New Photochemical and Electrochemical Methods for the Degradation of Pesticides in Aqueous media. Environmental Applications, Turk J Chem. 25 (2001), 509-520.*

* cited by examiner

*Primary Examiner* — Vasu Jagannathan
*Assistant Examiner* — Robert C Boyle
(74) *Attorney, Agent, or Firm* — Young & Thompson

(57) ABSTRACT

The present invention concerns the use of RO. radicals, R being a hydrogen, an alkyl group having 2 to 15 carbons, an acyl group —COR' in which R' represents an alkyl group having 2 to 15 carbons, or an aroyl group —COAr in which Ar represents an aromatic group having 6 to 15 carbons, for the hydroxylation, alkoxylation or oxycarbonylation of polymer surfaces, the said polymers being different from polymers chosen from: polymethylmethacrylate (PMMA) and fluorocarbon polymers when R represents a hydrogen, or of polymer mixture surfaces, notably hydrophobic ones, the said polymers consisting in monomeric units of which at least 50% among these are aliphatic units, and the said RO. radicals being generated by electrochemical or photochemical means.

14 Claims, No Drawings

MODIFICATION PROCESS FOR POLYMER SURFACES, NOTABLY FOR HYDROXYLATION OF POLYMER SURFACES AND PRODUCTS SO OBTAINED

The object of the present invention concerns a modification process of polymer surfaces, and notably a hydroxylation process of polymer surfaces, as well as the surfaces so modified.

Electrografting allows the functionalisation of electrical conducting and semi-conducting surfaces. One of the main benefits of electrografting is the energy that allows both the formation of interfacial bonds and the growth of films on the surface: therefore, it is the surface itself which generates its own functionalisation. This property has, for example, for consequence that the electrografted layers fill with great precision the surface topology on which they have been carried out, and even on a nanometric scale. On a macroscopic scale, it also has for consequence that the electrografting delivers coatings on pieces having an arbitrary complex form with an even quality throughout: everywhere where the surface is wet by the electrografting solution, there will be an electrografted film formed.

It is clearly impossible to carry out electrografting on insulant surfaces, at least under its usual form, given that the direct activation of the insulant by its nature is impossible by electrical means.

In order to propose functionalisations of similar quality on any type of surfaces, it is necessary to develop grafting processes on insulants, by searching—either in the molecular precursors, or in the surface activation techniques—specificities which allow to maintain the essential elements needed for the electrografting: interfacial bonding (covalent or non-covalent), conformity, homogeneity . . . .

It is interesting to functionalise the polymer surfaces to impart them with specific properties of hydrophily, hydrophoby, adsorption or non-adsorption of proteins or other biological molecules, binding of any types of organic or inorganic materials, adherence, more generally any desirable property for the desired application and being able to refer to a modification of functions offered by the surface of the considered object. This can be realised directly or by post-functionalisation, after initial treatment destined to make the surface more reactive.

An object of the present invention is to provide a process for the preparation of modified surfaces from polymer surfaces, particularly by use of OH. or OR. radicals.

A further object of the present invention is to provide modified polymer surfaces, particularly made hydrophilic, being able after to be used in subsequent functionalisation reactions.

The present invention concerns the use of RO. radicals, R being a hydrogen, an alkyl group having 2 to 15 carbons, an acyl group —COR' in which R' represents an alkyl group having 2 to 15 carbons, or an aroyl group —COAr in which Ar represents an aromatic group having 6 to 15 carbons, for the hydroxylation, alkoxylation or oxycarbonylation of polymer surfaces, the said polymers being different from polymers chosen from: polymethylmethacrylate (PMMA) and fluorocarbon polymers when R represents a hydrogen, or polymer mixture surfaces particularly hydrophobic ones, the said polymers consisting in monomeric units of which at least 50% among these are aliphatic units and the said RO. radicals being generated by electrochemical or photochemical means.

The present invention also concerns the use of HO. hydroxyl radicals, for the hydroxylation of hydrophobic polymer surfaces, the said polymers consisting in monomeric units of which at least 50% among these are aliphatic units and being different from polymers chosen from: polymethylmethacrylate (PMMA) and fluorocarbon polymers.

The term "surface hydroxylation" means the binding of hydroxyl groups (—OH) on the said surfaces.

The term "surface alkoxylation" means the binding of alkoxy groups (—OR) on the said surfaces, R being an alkyl group as defined above.

The term "surface oxycarbonylation" means the binding of oxycarbonyl groups (—OCOR' or —OCOAr, R' and Ar being as defined above) on the said surfaces.

The term "polymer mixtures" means a material obtained by mixing at least two polymers. For example, the polymer Acrylonitrile-Butadiene-Styrene is a material obtained by dispersing a grafted elastomeric phase (butadiene) in a styrene phase: styrene-acrylonitrile copolymer.

The term "monomeric units" means the repetitive units in the polymer.

The term "aliphatic units" means units not containing aromatic groups, i.e. cyclic groups containing 4n+2 electrons delocalised in the entire cycle.

According to a preferred embodiment, the hydrophobic polymers to which is applied the hydroxylation process of the invention are polymers whose atoms on the main chain: carbon, nitrogen or oxygen, are not bound by single bonds.

The term "main chain" means the longest chain that it is possible to find on a polymeric chain.

According to a preferred embodiment, the hydrophobic polymers to which is applied the hydroxylation process of the invention are polymers whose atoms on the main chain: carbon, nitrogen or oxygen, are not bound by single bonds, the substituents of side chains not being carboxylic groups or their esters or fluorine atoms, but being preferably hydrogen atoms, alkyl groups having 1 to 6 carbons, aryl groups having 6 to 14 carbons, et eventually heteroatoms chosen from: N, O and S, cyano groups or chlorine atoms.

According to a preferred embodiment, the hydrophobic polymers to which is applied the hydroxylation process of the invention are not silicon polymers.

The present invention also concerns the use of the Fenton reaction, for the hydroxylation, alkoxylation or oxycarbonylation of polymer surface, the hydroxylation reaction being carried out on polymers different from polymers chosen from: polymethylmethacrylate (PMMA) and fluorocarbon polymers, or polymer mixture surfaces, the said polymers consisting in monomeric units of which at least 50% among these are aliphatic units, the Fenton reaction being carried out by electrochemical or photochemical means.

The term "Fenton reaction" means a reaction which allows to produce hydroxyl radicals by reaction of hydrogen peroxide with iron (II).

This reaction can be represented by the following reaction scheme:

$$Fe^{2+}+H_2O_2+H^+ \rightarrow Fe^{3+}+H_2O+HO^\circ \quad k=55 M^{-1}s^{-1}$$

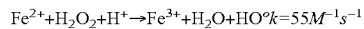

The reaction is particularly described in the following articles: Fenton, H., J., H. *J. Chem. Soc.* 1894, 65, 899; Haber, F.; Weiss, *J. Proc. Roy. Soc. A.* 1934, 134, 332 Barb.; W. G.; Baxendale, J., H.; George, P.; Hargrave, K. R. *Nature* 1949, 163, 692 Walling, C.; Weil, T. *Int. J. Chem. Kinet.* 1974, 6, 507; Gallard, H.; DeLaat, J.; Legube, B. *Wat. Res.* 1999, 33, 2929.

This reaction has also been applied, in the scope of the current invention, by replacing hydrogen peroxide with a peroxide ROOR, R being as defined above.

The use of the Fenton reaction for surface hydroxylation, alkoxylation or oxycarbonylation allows to obtain hydroxyl, alcoxy or oxycarbonyle radicals in a simplest way than notably plasma or gamma radiation treatments.

It is particularly advantageous to use the Fenton, ElectroFenton and PhotoFenton reactions because they are applicable to polymers independently of their chemical structure: the reactions are therefore nonspecific of the chemical structures of the polymers.

According to an advantageous embodiment, the present invention concerns the use such as defined above, characterised in that the Fenton reaction is realised by electrochemical means, i.e. by the use of the ElectroFenton reaction.

The ElectroFenton reaction allows to continuously produce hydroxyl radicals by continually regenerating $Fe^{2+}$ at the cathode and by reducing dioxygen to hydrogen peroxide at the same cathode. This variant of the Fenton reaction allows to produce large quantities of radicals by living on the electrolysis for a sufficient amount of time.

The ElectroFenton reaction (Tomat, R.; Vecchi, A. *J. Appl. Electrochem.* 1971, 1, 185; Oturan, M. A.; Pinson, *J. New J. Chem* 1992, 16, 705; Fang, X.; Pam, X.; Rahman, A. P. *Chem. Eur. J.* 1995, 1, 423; Gallard, H.; DeLaat, *J. Chemosphere* 2001, 42, 405; Matsue. T., Fujihira, M.; Osa, T. *J. Electrochem. Soc.* 1981, 128, 2565; Fleszar, B.; Sobkoviak, A. *Electrochim. Act.* 1983, 28, 1315; Tzedakis, T.; Savall, A.; Clifton, M., J. *J. Appl. Electrochem.* 1989, 19, 911; Oturan, M. A.; Oturan, N.; Lahitte, C.; Trévin, S. *J. Electranal. Chem.* 2001, 507, 96; Brillas, E.; Casado, J. *Chemosphere* 2002, 47, 241) is a variant of the Fenton reaction and consists of a catalytic reaction where $Fe^{2+}$ is regenerated continuously at the cathode at the same time as oxygen is reduced to give hydrogen peroxide.

The catalytic cycle is described below:

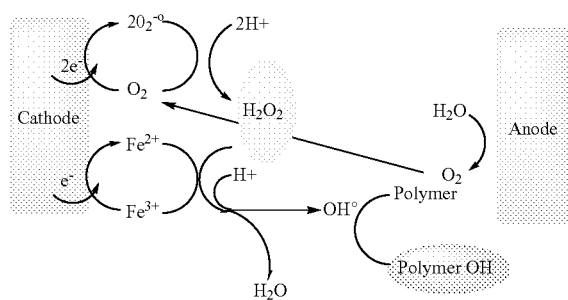

In addition, regarding the process of the present invention, the surface oxycarbonylation has been carried out by introducing directly in the electrolysis cell the peroxide and this without deoxygenation of the solution.

According to another advantageous embodiment, the present invention concerns the use as defined above, characterised in that the Fenton reaction is realised by photochemical means, i.e. by the use of the PhotoFenton reaction.

The PhotoFenton reaction (Brillas, E.; Sauleda, R.; Casado, J. *J. Electrochem. Soc.* 1998, 145, 759) is a variant of the Fenton reaction, corresponding to the following mechanism:

$$H_2O_2 + Fe^{2+} + H^+ \rightarrow Fe^{3+} + H_2O + HO^\circ$$

$$Fe^{3+} + H_2O + h\nu \rightarrow Fe^{2+} + HO^{\circ} + H^+$$

$$H_2O_2 + h\nu \rightarrow 2OH^\circ$$

The PhotoFenton reaction allows to produce hydroxyl radicals by radiation of an aqueous solution of hydrogen peroxide and Fe(II). This reaction continuously regenerates Fe(II) and therefore allows hydroxyl radicals as long there is hydrogen peroxide. II therefore allows to continuously produce hydroxyl radicals.

The present invention also concerns a hydroxylation, alkoxylation or oxycarbonylation process of a polymer surface, the said polymers being different form polymers chosen from: polymethylmethacrylate (PMMA) and fluorocarbon polymers regarding the hydroxylation process, or polymer mixture surface, the said polymers consisting in monomeric units of which at least 50% among these are aliphatic units, to obtain a hydroxylated, alkoxylated or oxycarbonylated surface, the said process being characterised in that it consists of reacting the said surface with RO. radicals, R being a hydrogen, an alkyl group having 2 to 15 carbons, an acyl group —COR' in which R' represents an alkyl group having 2 to 15 carbons, and in particular a butyl or lauryl group, or an aroyl group —COAr in which Ar represents an aromatic group having 6 to 15 carbons, in particular a phenyl group, the said RO. radicals being generated by electrochemical or photochemical means.

The term "hydroxylated surface" means a surface containing hydroxyl groups (—OH).

The term "alkoxylated surface" means a surface containing alkoxy groups (—OR), R representing an alkyl group as defined above.

The term "oxycarbonylated surface" means a surface containing oxycarbonyl groups (—OCOR' or —OCOAr, R' and Ar being as defined above).

According to a particular embodiment, the oxycarbonalyted surfaces obtained according to the process of the invention contain —COR' or —COAr groups, R' and Ar being as defined above.

The RO. radicals are obtained by cleavage of RO—OR peroxide catalysed by Iron (II).

The HO, radicals are formed by cleavage par hydrogen peroxide 11202 catalysed by Iron (II).

A preferred hydroxylation process according to the invention is characterised in that it involves reacting the surface with HO. hydroxyl radicals.

The present invention also concerns a hydroxylation process of polymer surfaces, particularly hydrophobic ones, the said polymers consisting in monomeric units of which at least 50% among these are alkane units, to obtain a hydroxylated surface, the said process being characterised in that it involves reacting the said surface with HO. hydroxyl radicals obtained by the Fenton reaction, by electrochemical or photochemical means (ElectroFenton or PhotoFenton reaction).

The present invention concerns the process as defined above, characterised in that the HO. hydroxyl radicals are obtained by mixing hydrogen peroxide and ferric ($Fe^{3+}$) or ferrous ($Fe^{2+}$) ions.

According to an advantageous embodiment, the process of the invention is characterised in that the HO. hydroxyl radicals are obtained by the use of the ElectroFenton reaction.

According to an advantageous embodiment, the process of the invention, including the use of the ElectroFenton reaction, is characterised in that hydrogen peroxide is obtained directly by the electrochemical reduction of oxygen in an acidic medium, and in that the HO, hydroxyl radicals are provided from the reaction of ferrous ions with hydrogen peroxide.

The term "electrochemical reduction of oxygen" means the transfer of two electrons and two protons to oxygen to give hydrogen peroxide.

The term "acidic medium" means a medium where the pH is below 7 more particularly is between 2 and 4, more precisely equal to 3.

The present invention also concerns a process as defined above characterised in that the HO. hydroxyl radicals are obtained by the use of the PhotoFenton reaction.

According to an advantageous embodiment, concerning the use of the PhotoFenton reaction, the process of the invention is characterised in that the hydrogen peroxide is added to the polymer surface, and in that the HO. hydroxyl radicals are obtained by putting into contact the said surface with an aqueous solution containing hydrogen peroxide and a ferrous salt, particularly iron chloride or sulfate, and by irradiation of the said surface and the said solution.

The term "irradiation of the said surface and the said solution" means the fact to illuminate the solution and the surface(s) with a lamp emitting appropriate wavelengths, particularly in the ultraviolet region, i.e. wavelengths below 400 nm.

According to another advantageous embodiment, the present invention concerns the process as defined above, characterised in that the polymers are immerged in an aqueous solution containing hydrogen peroxide and a ferrous salt, particularly iron chloride or sulfate, and in that the said solution and the polymers are irradiated with a UV lamp.

The present invention also concerns the process as defined above, characterised in that the polymers contain monomeric units having a molecular weight from about 500 to about 5 millions daltons.

A molecular weight of 500 daltons corresponds to the lower limit of polymer molecular weights and a molecular weight of 5 million daltons corresponds to the mass of UHMW polyethylene (UltraHigh Molecular Weight).

The present invention also concerns a process as defined above, characterised in that ies polymers are chosen from: polyethylene, polypropylene, polyisobutylene (P-IB), polymethylpentene, polyvinyl chloride (PVC), polyvinyl acetate (PVAC), polyvinyl butyral (PVB), polyvinyl formal (PVFM), polyvinyl alcohol (PVAL), different polyamides, polyoxomethylenes (POM), cellulose derivatives et polyacrylonitrile (PAN).

The preferred polymers for the process of the invention are chosen from:

| Polymère | Motif |
|---|---|
| Polyethylene | $-(CH_2)_n-$ |
| Polypropylene | $-[CH_2-CH]_n-$ with $CH_3$ |
| Polyisobutylene | $-[CH_2-C(CH_3)_2]_n-$ |
| Polymethylpentene | $-[CH_2-CH(CH_2-CH(CH_3)_2)]_n-$ |
| Polyvinyl chloride | $-[CH_2-CHCl]_n-$ |
| Polyvinyl acetate | $-[CH_2-CH(OCOCH_3)]_n-$ |
| Polyacrylonitrile | $-[CH_2-CH(CN)]_n-$ |
| Polyvinyl alcohol | $-[CH_2-CH(OH)]_n-$ |
| Polyvinyl butyral | $-[CH(O)-CH_2-CH(O)-CH_2]_n-$ with $CH(CH_2CH_2CH_3)$ bridge |
| Polyvinyl formal | $-[CH(O)-CH_2-CH(O)-CH_2]_n-$ with $CH_2$ bridge |
| Polyoxymethylene | $-[CH_2-O]_n-$ |
| Polyamide | $-[NH-(CH_2)_6-NH-CO-(CH_2)_8-CO]_n-$ |

Preferably, the polymers used for the process of the invention are polyolefins which are polymers obtained by olefin polymerisation, i.e. compounds having at least one double bond which can be broken to lead to the polymerisation.

Preferably, the polymers involved in the invention are different form polysiloxanes polymers.

The present invention also concerns a process as defined above, characterised in that les polymers are composed of monomeric unit having at least one aromatic unit, in particular a pendant aryl group, and at least an alkane unit, the said polymers being chosen from: random copolymers, alternate copolymers et block copolymers (diblock, triblock, multiblock or radial).

Alternate copolymers are polymers of the form: -ABABABAB-.

Block or sequential copolymers are polymers of the form -AAAAAABBBBBBAAAAAABBBBBBB- or -AAAAAABBBBBBCCCCCCAAAAAABBBBBB- Random copolymers are polymers of the form: -AABABBAAABABB- Bisequential copolymers are polymers of the form: $-(A)_n-(B)_t-$ Trisequential copolymers are polymers of the form: $-(A)_m-(B)_n-(A)_t-$ Star copolymers (or radical) are polymers of the form:

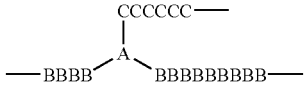

A, B and C representing monomeric units as defined above.

The present invention also concerns the process as defined above, characterised in that the polymer surface is in the form of a sheet, a knitted material, a tube, for example a catheter, strands, nails or screws, balls, objects of different forms being able to serve as prostheses or extra or intraocular lenses.

According to a preferred embodiment, the process of the invention is characterised in that it does not include a reticulation step.

The present invention also concerns a process as defined above, characterised in that the step to react HO. hydroxyl radicals is carried out for about 5 minutes to about 5 hours.

The present invention also concerns a process as defined above, characterised in that it includes a subsequent functionalisation step on the hydroxyl groups bound on the polymer surface.

Among the subsequent functionalisation reactions, one can cite: the formation of esters by reaction with a carboxylic acid, ethers by Williamson reaction with another alcohol, halides by reaction with halide acids or $PCl_5$, N-alkylamides by Mitsunobu reaction or sulfides by reaction with thiols.

Generally, post-functionnalisation allows one skilled in the art to place an organic function of choice on the surface for a targeted application, for example in the biomedical domain, adhesion and non-adhesion proteins, binding of pharmaceutical substances, antimicrobials.

Subsequent functionalisation reactions allow to give specific properties on the surface: for example by binding biologically-active molecules (for example, enzymes) or molecules having pharmaceutical properties. This can be carried out by binding the OH group on the surface either directly to the desired molecule or by an intermediate on an intermediate linkage. One can link alcoholic functionality by ester formation (by reaction with an anhydride, an acid chloride or even an acid), amide formation (by reaction with isocyanates) or ether formation (by reaction with alkyl halides).

The present invention also concerns a hydroxylation process as defined below, characterised in that the contact angle measured between the drop of water and the hydroxylated surface obtained decreases to more than 5°, particularly, to more than 10° relative to the contact angle measured between a drop of water and a non-hydroxylated surface.

The contact angle is measured by depositing a drop of water on the polymer surface with a syringe, then measuring with the help of a microscope the angle formed between the polymer surface and the tangent of the drop by its contact point with the polymer.

The more the surface is hydrophilic, the more the measured contact angle is small, and the more the surface is hydrophobic, the more the measured contact angle is large.

The present invention also concerns a process as defined above, characterised in that the hydroxylated, alkoxylated or oxycarbonylated surfaces obtained are time stable, particularly during many weeks, according to the following test:

The infrared spectra of PET and PEEK samples, modified by a ElectroFenton reaction either during 10 minutes, or during 120 minutes, then trifluoroacetylated, are re-recorded after 74 days. By recording the spectral differences (t=0 and t=74 days), no significant differences and in particular no disappearance of characteristic bands corresponding to trifluoroacetyl groups are noted.

The present invention also concerns hydroxylated, alkoxylated or oxycarbonylated surfaces obtained by the use of the process of the invention as defined above.

As shown by the measurement of the contact angles reported in the following experimental part, the treated surfaces according to the hydroxylation process of the present invention have become hydrophilic and will be consequentially much more bio-compatible.

The bond between the polymer and the OH group is a covalent bond whose energy is in the range of 390 ($CH_3OH$) to 470 kJ/mol ($C_6H_5OH$).

I—Electro-Fenton Reaction
Hydroxylation of Polypropylene (PP)
Of Polyethylene (PE) and
Of Acrylonitrile-Butadiene-Styrene (ABS)
Substrates—knitted PP and
—Goodfellow PP301400 sheet
—very high molecular weight PE (sheet) (Goodfellow ET301400)
ABS plate (Goodfellow, AB3030090) [obtained by dispersing an elastomeric phase (butadiene) in a styrene phase (SAN) obtained by copolymerisation of acrylonitrile with styrene]
Electrochemical Device:
Non-separated compartment cell.
Anode: carbon.
Cathode: carbon felt (approximately 10 $cm^2$).
The polymer sheet or knitted material was tightened against one sheet or placed between two carbon felt sheets serving as the cathode.
Solvent 0.1M $H_2SO_4$ brought to pH 3 with sodium hydroxide
Catalyser 0.5 mM $Fe^{2+}$ ($FeSO_4 . 7H_2O$)
Continuous Air Bubbling
Galvanostatic method: Constant current: 10 mA or 5 mA according to the experiment
Potentiostatic method: Constant potential E=−0.6V/SCE
A) Hydroxylation of PP
Hydroxylation of a PP sheet (Goodfellow)
By galvanostatic i=5 mA, 2 hours, the counter-electrode was short-circuited on the reference. The cathode potential was increased from approximately −0.6V/SCE at the beginning of the experiment to approximately −2V/SCE at the end of the electrolysis, at this potential the protons were reduced and therefore the reduction efficiency of oxygen was reduced. The samples were carefully rinsed with distilled water during 10 minutes under sonication, then 10 minutes in acetonitrile (for analysis) and dried at 40° C. under vacuum overnight.

By potentiostatic, the current decreased from approximately 30 to 10 mA. The samples were treated as described above.

For IR analysis, the samples were treated with a solution of trifluoroacetic anhydride (1 mL) in ether (30 mL) overnight, rinsed with acetonitrile then dried under vacuum overnight. The results are shown in Table 1.

TABLE 1

IR analysis of a hydroxylated then trifluoroacetylated PP sheet*

| Band positions in $cm^{-1}$ | Attribution | By comparison |
|---|---|---|
| 1794 | C=O | ≈1813 $cm^{-1}$ for $(CF_3CO)_2O$ |
|  |  | ≈1780 $cm^{-1}$ for $CF_3COOH$ |
| 1206 | $CF_3$ | ≈1160, 1240 $cm^{-1}$ for $(CF_3CO)_2O$ |
| 1179 |  | ≈1190, 1240 $cm^{-1}$ for $CF_3COOH$ |

Reference: non-treated PP sheet.

The $CF_3$ band was larger on the spectrum corresponding to potentiostatic electrolysis than galvanostatic electrolysis, it seemed that the yield was greater with potentiostatic, however, there was no difference regarding the band position.

The ToF-SIMS analysis confirmed well the surface trifluoromethylation

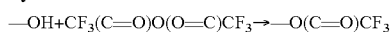

(see fragments described in Table 2 below).

TABLE 2

ToF-SIMS analysis of a hydroxylated
then trifluoroacetylated PP sheet

| m/z | Attribution[a] |
|---|---|
| 19 | $F^-$ |
| 97 | $C(=O)CF_3^-$ or $CH_2CH_2CF_3^{-[b]}$ |
| 113 | $OC(=O)CF_3^-$ |
| 69 | $CF_3^+$ |
| 95 | $CH=CHCF_3^+$ |
| 97 | $CH_2CH_2CF_3^+$ or $C(=O)CF_3^{-[b]}$ |
| 109 | $CH_2CH=CHCF_3^+$ |
| 111 | $CH_2CH_2CH_2CF_3^{+[b]}$ |
| 123 | $CH_2CH_2CH=CHCF_3^{+[b]}$ |
| 125 | $CH_2CH_2CH_2CH_2CF_3^{+[b]}$ |
| 147 | $C=CCH_2CH_2CH=CHCF_3^{+[b]}$ |
| 207 | $CH_2(CH_2)_5CH=CHCF_3^{+[b]}$ |
| 221 | $CH_2(CH_2)_6CH=CHCF_3^{+[b]}$ |

[a]or isomer,
[b]$CH_2CH_2$ and $C=O$ having the same mass, it would be possible to write the ions m/z = 97 (positives et negatives) under the two isomeric forms indicated. The negative ion is attributed to the trifluoroacetyl group. For the positive ion, the presence of ion at m/z = 95 seemed to indicate the loss of two hydrogens and therefore allowed to attribute the peak to the trifluoroethyl ion.

The presence of trifluoromethyl groups (ant in particular trifluoromethylated alkyl chains) confirmed that the surface was well hydroxylated then trichloromethylated. However, during the analysis there was probably a rearrangement of ions with the loss of $CO_2$ as no fragments of type $(CH_2)_nOC(=O)CF_3$ were observed.

Analysis of the contact angle of water measured with non-treated PP was 124°, after treatment it decreased to 102° immediately after the deposit of the drop, et continued to slowly decrease after: 73° after 10 and 20 minutes (without notable evaporation of the drop).

Hydroxylation of Knitted Material

Electrolysis 1 hour. Galvanostatic method: i=10 mA

IR analysis of the surface showed, by difference with a non-treated sample, a band at 3419 cm$^{-1}$ which corresponded to a OH stretching vibration, a weak band at 1037 cm$^{-1}$ could be attributed to a C—OH deformation.

By ToF-SIMS, O and OH peaks observed were clearly larger than on the reference as well as the peaks non present on the reference shown in Table 3.

TABLE 3

Analysis of hydroxylated knitted Sofradim by ToF-SIMS

| m/z | Attribution |
|---|---|
| 32 | $CH_3O^-$ |
| 60 | $HO—HC=CH—OH^-$ |
| 79 | $C_5H_3OH^-$ |
| 113 | $C_7H_{13}OH^-$ |

After trifluoromethylation, fluorinated peaks were observed: $F^-$, $CF_3^-$, $OCOCF_3^-$, $C_7H_{15}OCOCF_3^-$. This latter peak was particularly interesting, it contained a part of the polymer and the OH function which had been tritluoroacetylated, showing therefore that the OH function was well covalently attached to the surface. Few differences were observed between the sheet and knitted material spectra, this could be due either to the reproducibility of the experiments, or a different reactivity of the two substrates even tough they had an identical chemical composition.

On the knitted material, the contact angle was very difficult to measure, however, after hydroxylation, the water drop passed through the surface.

B) Hydroxylation of PE

Surface modification was realised in a solution of 0.1N sulfuric acid brought to pH 3 by the addition of sodium hydroxide, in presence of 0.5 mM $FeSO_4$, with air bubbling, in a potentiostatic mode at −0.6 V/SCE for 2 hours.

The contact angle with water was measured before and after grafting: it went from about 91° to about 70°. This showed well that the polypropylene surface had been hydroxylated.

The IR spectrum of the hydroxylated surface was recorded.

TABLE 4

IR spectrum of PE after treatment*

| Band position in cm$^{-1}$ | Attribution |
|---|---|
| 3310 | O—H |
| 1047 | C—O primary alcohol |

*after subtraction of the non-treated reference, the samples were dried under vacuum at 40° C. for two days, to assure that the OH bands did not come from superficial humidity.

The sample was trifluoroacetylated as above. To obtain a reference, the trifluoracetylation treatment was carried out on a sample which had not been hydroxylated.

TABLE 5

IR analysis of a hydroxylated then trifluoroacetylated PE sheet*

| Band position in cm$^{-1}$ | Attribution | By comparison |
|---|---|---|
| 1742 | C=O | ≈1813 cm$^{-1}$ for $(CF_3CO)_2O$ |
|  |  | ≈1780 cm$^{-1}$ for $CF_3COOH$ |
| 1240 | CF3 | ≈1160, 1240 cm$^{-1}$ for $(CF_3CO)_2O$ |
| 1170 |  | ≈1190, 1240 cm$^{-1}$ for $CF_3COOH$ |

Reference: non-hydroxylated PE sheet subjected to trifluoroacetylated treatment.

TABLE 6

ToF-SIMS analysis of a hydroxylated then
trifluoroacetylated PE sheet

| m/z | Attribution |
|---|---|
| 19 | F– |
| 69 | $CF_3^-$; $CF_3^+$ |
| 97 | $C(=O)CF_3^-$; $C(=O)CF_3^+$ |
| 113 | $OC(=O)CF_3^-$ |
| 119 | $(CH_2)_2CF_2H^-$ |
| 131 | $C_3H_4OC(=O)CF_3^+$ |
| 155 | $(CH_2)_3OC(=O)CF_3^+$ |
| 169 | $(CH_2)_4OC(=O)CF_3^+$ |
| 181 | $C_5H_8OC(=O)CF_3^+$ |
| 193 | $C_6H_8OC(=O)CF_3^+$ |
| 265 | $CH_3(CH_2)_{10}OC(=O)CF_3^-$ |

The variation of the contact angle, the IR spectra et more particularly the ToF-SIMS spectra showing the AlkylOC(=O)CF$_3$ fragments, demonstrated well the hydroxylation and the post-functionalisation of the surface.

C) Hydroxylation of ABS

Under the same conditions as PE.

The contact angle with water was measured before and after grafting: it went from about 69° to about 37°.

The IR spectrum of the hydroxylated surface was recorded.

TABLE 7

IR spectrum of ABS after treatment.

| Band position in cm$^{-1}$ | Attribution |
|---|---|
| 3240 | O—H |
| 1050 | C—O primary alcohol |

*after subtraction of a non-treated reference, the samples were dried under vacuum at 40° C. for 2 days to assure that the OH bands did not come from residual humidity.

The sample was trifluoroacetylated as above. To obtain a reference, the trifluoroacetylation treatment was carried out on a sample which had not been hydroxylated.

TABLE 8

IR analysis of a hydroxylated then trifluoroacetylated ABS sheet*

| Band Position in cm$^{-1}$ | Attribution | By comparison |
|---|---|---|
| 1765 | C=O | ≈1813 cm$^{-1}$ for (CF$_3$CO)$_2$O |
|  |  | ≈1780 cm$^{-1}$ for CF$_3$COOH |
| 1245 shouldering | CF3 | ≈1160, 1240 cm$^{-1}$ for (CF$_3$CO)$_2$O |
| 1160 shouldering |  | ≈1190, 1240 cm$^{-1}$ for CF$_3$COOH |

Reference: non-hydroxylated ABS sheet and subjected to trifluoroacetylation treatment.

TABLE 9

ToF-SIMS analysis of a hydroxylated then trifluoroacetylated ABS sheet*

| m/z | Attribution |
|---|---|
| 19 | F$^-$ |
| 69 | CF3$^-$ |
| 97 | C(=O)CF3$^-$ |
| 145 | OC(=O)CF3$^-$ |
| 228 | NC—(CH$_2$)$_5$—OC(=O)CF$_3$$^+$ |

Grafting Stability as a Function of Time

After 74 days, the infrared spectra of a PP sample modified by the electroFenton reaction either for 10 minutes, or for 120 minutes then trifluoroacetylated were recorded. By recording the difference between the spectra (t=0 and t=74 days), no significant differences and in particular no disappearance of the characteristic trifluoroacetyl group bands were observed.

II—Photo-Fenton Reaction

Hydroxylation of Polypropylene (PP)

Of Polyethylene (PE) and

Of Acrylonitrile-Butadiene-Styrene (ABS)

A) Hydroxylation of Polypropylene (PP)

A 2 L glass reactor equipped with a circulation pump, a thermostated double-jacket and a low pressure mercury lamp placed in the middle of the reactor in a quartz tube was filled with 2 L of a 1 mM HCl solution in water, 1 g of ferric chloride and 2 mL of hydrogen peroxide. The polymer samples were suspended in the solution. The pump and irradiation were started; after 2 h 30, the irradiation was stopped. The samples were rinsed for 15 minutes with distilled water under sonication then with acetone and dried under vacuum at 40° C. overnight.

IR analysis of the samples allowed to see the attributable bands of OH groups at 3343 and 3230 cm$^{-1}$ (after subtraction of the PP spectrum itself).

The calculation of contact angles with water was carried out before and after treatment.

TABLE 10

Contact angles of polymer samples treated by PhotoFenton.

| Sample | Contact angle before treatment | Contact angle after treatment |
|---|---|---|
| PP | 124 | 124[a] |
|  |  | 86 (after 10')[b] |
|  |  | 80 (after 20') |

[a] Immediately after the deposit of the drop
[b] without notable decrease in the drop size.

The samples were then treated with trifluoroacetic anhydride (0.4 mL in 10 mL of ether) and analysed by IR. Bands towards 1206-1254 cm$^{-1}$ and 1165-1185 cm$^{-1}$ were well observed, which were attributed to the group CF$_3$ vibrations by comparison with the spectra of trifluoroacetic acid and trifluoroacetic anhydride. The vibration corresponding to the carbonyl group (C=O)CF$_3$ was observable. These spectra confirmed well the modification on the polymer surface.

TABLE 11

IR spectra of the trifluoroacetylated samples.

| Sample | IR Absorption in cm$^{-1}$ | Attribution |
|---|---|---|
| PP[a] | ≈1800 vw | C=O (≈1790 cm$^{-1}$ for CF$_3$COOH) |
|  | 1206 s | CF$_3$ (1248 for CF3CO)$_2$O and 1240 for CF$_3$COOH) |
|  | 1166 m | CF$_3$ (1195 for CF3CO)$_2$O and 1177 for CF$_3$COOH) |

TABLE 12

ToF-SIMS spectra of trifluoroacetylated samples

| Sample | m/z | Attribution |
|---|---|---|
| PP[a] | 19 | F$^-$ |
|  | 69 | CF$_3$$^-$, CF$_3$$^+$ |
|  | 113 | [O(C=O)CF$_3$]$^-$ |
|  | 182 | [CF$_3$(C=O)OCHCH$_3$CH$_2$CCH$_3$]$^-$ |

The ToF-SIMS spectra confirmed well the polymer grafting by the OCF$_3$ groups after treatment with acetic anhydride, therefore surface hydroxylation.

B) Hydroxylation of Polyethylene (PE)

The hydroxylation and the trifluoroacetylation were carried out under the same conditions as for polypropylene. The samples were analysed by ToF-SIMS.

TABLE 13

ToF-SIMS spectra of trifluoroacetylated samples.

| Sample | m/z | Attribution |
|---|---|---|
| PE[a] | 19 | F$^-$ |
|  | 69 | CF$_3$$^-$, CF$_3$$^+$ |
|  | 97 | C(=O)CF$_3$$^-$ |
|  | 113 | [O(C=O)CF$_3$]$^-$ |
|  | 182 | [CF$_3$(C=O)OCH(CH$_2$)$_4$]$^-$ |

Table 13 showed well the polyethylene grafting by OH groups and the subsequent trifluoroacetylations. In particular, the fragment at m/z—182 represented a fragment of PE chain containing a trifluoroacetyl group.

C) Hydroxylation of ABS

Under the same conditions as for PP, the samples were analysed by ToF-SIMS.

TABLE 14

ToF-SIMS spectra of trifluoroacetylated samples.

| Sample | m/z | Attribution |
|---|---|---|
| PE$^a$ | 19 | F$^-$ |
| | 69 | CF$_3^-$, CF$_3^+$ |
| | 97 | C(=O)CF$_3^-$ |
| | 113 | [O(C=O)CF$_3$]$^-$ |
| | 207 | OC(=O)CF$_3$ |

The spectrum confirmed well the hydroxylation and trifluoroacetylation of ABS.

Analogous Reaction to the Fenton Reaction, Using Benzoyl Peroxide

In this reaction, hydrogen peroxide was replaced by benzoyl peroxide. Two samples of PP and PE were enveloped in carbon felt, and these coatings were used as the cathode. A solution was prepared by introducing 400 mg of benzoyl peroxide (saturated solution) and 55 mg of FeSO$_4$, 7H$_2$O in 400 ml of a 0.1N H$_2$SO$_4$ solution brought to pH 3 by the addition of sodium hydroxide. The solution was deoxygenated with argon. The potential was fixed at E=−0.6 V/SCE for 2 hours. The samples were then rinsed with tap water, twice with distilled water under sonication (10 minutes), then once with acetone under sonication and dried under vacuum.

The samples were analysed by ToF-SIMS.

TABLE 15

ToF-SIMS spectra of samples treated with benzoyl peroxide under the conditions of the Fenton reaction.

| m/z | Attribution |
|---|---|
| PE | |
| 105 | C$_6$H$_5$C(=O)$^+$ |
| 120 | C$_6$H$_5$C(=O)CH$_3^+$ |
| 163 | C$_6$H$_5$C(=O)(CH2)$_3^+$ |
| PP | C$_6$H$_5$C(=O)$^+$ |
| 105 | |
| 147 | CH$_2$CH(CH$_3$)C(=O)C$_6$H$_5^-$ |
| 207 | CH$_3$CH(CH$_3$)CH$_2$CH(CH$_3$)OC(=O)C$_6$H$_5$ |

Table 15 showed well the grafting by C$_6$H$_5$C(=O) or C$_6$H$_5$C(=O)O groups for PE and PP.

The invention claimed is:

1. A method for hydroxylation, alkoxylation or oxycarbonylation of polymer surfaces, comprising:
   obtaining photochemical Fenton reaction-derived RO. radicals,
   reacting said polymer surfaces with said RO. radicals, wherein
   R of said RO. radicals is selected from the group consisting of a hydrogen, an alkyl group having 2 to 15 carbon atoms, an acyl group —COR' in which R' represents an alkyl group having 2 to 15 carbon atoms, and a aroyle group —COAr in which Ar represents an aromatic group having 6 to 15 carbon atoms,
   said polymer surfaces being different from polymers selected from the group consisting of polymethylmethacrylate (PMMA) and fluorocarbon polymers when R represents a hydrogen, and polymer mixture surfaces,
   said polymer surfaces comprise monomeric units of which at least 50% among these are aliphatic units.

2. A method for hydroxylation, alkoxylation or oxycarbonylation of polymer surfaces, comprising:
   photochemically carrying out a Fenton reaction on said polymer surfaces,
   said reaction being carried out on polymer surfaces different from polymers selected from the group consisting of polymethylmethacrylate (PMMA), fluorocarbon polymers, and polymer mixture surfaces, and
   said polymer surfaces comprising monomeric units of which at least 50% among these are aliphatic units.

3. A process for hydroxylation, alkoxylation or oxycarbonylation of polymer surfaces, comprising:
   obtaining photochemical Fenton reaction-derived RO. radicals,
   reacting said polymer surfaces with said R. radicals, wherein
   said polymer surfaces being different from polymers selected from the group consisting of: polymethylmethacrylate (PMMA) and fluorocarbon polymers for the hydroxylation process, and polymer mixture surfaces, the said polymers comprising monomeric units of which at least 50% among these are aliphatic units, to obtain a hydroxylated, alkoxylated or oxycarbonylated surface, and
   said R of said RO. radicals selected from the group consisting of a hydrogen, an alkyl group having 2 to 15 carbon atoms, an acyl group —COR' in which R' represents an alkyl group having 2 to 15 carbon atoms, and an aroyl group —COAr in which Ar represents an aromatic group having 6 to 15 carbon atoms.

4. The process according to claim 3, wherein the RO. radicals are HO. hydroxyl radicals so that the process comprises reacting the polymer surfaces with HO. hydroxyl radicals.

5. The process according to claim 3, wherein the polymer surfaces contain monomeric units presenting a molecular weight from 500 to 5 million daltons.

6. The process according to claim 3, wherein the polymer surfaces are in a form selected from the group consisting of: a sheet, a knitted material, a tube, strands, nails or screws, balls, and objects of different forms being able to serve as prostheses or extra or intraocular lenses.

7. The process according to claim 3, wherein the step of reacting the polymer surfaces with the RO. radicals is carried out for 5 minutes to 5 hours.

8. The process according to claim 3 further comprising: subsequently functionalizing the hydroxyl groups linked to the hydroxylated surface.

9. A hydroxylation process of a polymer surface, comprising:
   obtaining PhotoFenton reaction-derived RO. radicals
   reacting said surface with said HO. hydroxyl radicals, wherein
   said polymer surface comprises monomeric units of which at least 50% among these are aliphatic units,
   said polymer surface is different from polymers selected from the group consisting of: polymethylmethacrylate (PMMA) and fluorocarbon polymers, to obtain a hydroxylated surface, and
   said polymer surface selected from the group consisting of: polyethylene, polypropylene, polyisobutylene (PIB), polymethylpentene, polyvinyl chloride (PVC), polyvinyl acetate (PVAC), polyvinyl butyral (PVB), polyvinyl formal (PVFM), polyvinyl alcohol (PVAL), different polyamides, polyoxomethylenes (POM), cellulose derivatives et polyacrylonitrile (PAN), and combinations thereof.

10. The process according to claim 9, wherein the step of obtaining the HO. hydroxyl radicals is carried out by mixing hydrogen peroxide and ferric ($Fe^{3+}$) or ferrous ($Fe^{2+}$) ions.

11. The process according to claim 9, wherein the polymers contain monomeric units presenting a molecular weight from 500 to 5 million daltons.

12. The process according to claim 9, wherein the surface of the polymers is in a form selected from the group consisting of: a sheet, a knitted material, a tube, strands, nails or screws, balls, and objects of different forms being able to serve as prostheses or extra or intraocular lenses.

13. The process according to claim 9, wherein the step of reacting the surface with the HO. hydroxyl radicals is carried out for 5 minutes to 5 hours.

14. The process according to claim 9 further comprising: subsequently functionalizing the hydroxyl groups linked to the hydroxylated surface.

\* \* \* \* \*

UNITED STATES PATENT AND TRADEMARK OFFICE
CERTIFICATE OF CORRECTION

| | |
|---|---|
| PATENT NO. | : 7,968,653 B2 |
| APPLICATION NO. | : 12/089960 |
| DATED | : June 28, 2011 |
| INVENTOR(S) | : Christophe Bureau and Jean Pinson |

It is certified that error appears in the above-identified patent and that said Letters Patent is hereby corrected as shown below:

In column 2, line 25 delete "not" and replace with -- only --.

In column 2, line 31 delete "not" and replace with -- only --.

Signed and Sealed this
Twenty-ninth Day of November, 2011

David J. Kappos
*Director of the United States Patent and Trademark Office*